US008738303B2

(12) United States Patent
Russak

(10) Patent No.: US 8,738,303 B2
(45) Date of Patent: May 27, 2014

(54) IDENTIFYING OUTLIERS AMONG CHEMICAL ASSAYS

(75) Inventor: Ze'ev Russak, Ramat Gan (IL)

(73) Assignee: Azure Vault Ltd., Ramat-Gan (IL)

(*) Notice: Subject to any disclaimer, the term of this patent is extended or adjusted under 35 U.S.C. 154(b) by 446 days.

(21) Appl. No.: 13/098,519

(22) Filed: May 2, 2011

(65) Prior Publication Data

US 2012/0283962 A1 Nov. 8, 2012

(51) Int. Cl.
*G06F 19/00* (2011.01)
*G06F 19/24* (2011.01)

(52) U.S. Cl.
USPC .................................. 702/32; 702/19; 702/22

(58) Field of Classification Search
CPC ......... G06F 19/24; G06F 19/28; G06F 19/70; G01N 30/8644
USPC ............................................... 702/19, 22, 32
See application file for complete search history.

(56) References Cited

U.S. PATENT DOCUMENTS

| | | | |
|---|---|---|---|
| 5,606,164 | A | 2/1997 | Price et al. |
| 6,289,328 | B2 | 9/2001 | Shaffer |
| 6,503,720 | B2 | 1/2003 | Wittwer et al. |
| 6,763,308 | B2 | 7/2004 | Chu et al. |
| 6,944,602 | B2 | 9/2005 | Cristianini |
| 7,050,932 | B2 | 5/2006 | Selby et al. |
| 7,062,415 | B2 | 6/2006 | Whitefield et al. |
| 7,523,384 | B2 | 4/2009 | Wold |
| 7,542,959 | B2 | 6/2009 | Barnhill et al. |
| 2003/0041041 | A1 | 2/2003 | Cristianini |
| 2003/0059837 | A1 | 3/2003 | Levinson et al. |
| 2003/0144746 | A1 | 7/2003 | Hsiung et al. |
| 2006/0004753 | A1 | 1/2006 | Coifman |
| 2006/0224330 | A1 | 10/2006 | Kurnik et al. |
| 2007/0021929 | A1 | 1/2007 | Lemmo et al. |
| 2007/0055477 | A1 | 3/2007 | Chickering et al. |
| 2007/0073489 | A1 | 3/2007 | Kurnik et al. |
| 2007/0073490 | A1 | 3/2007 | Kurnik et al. |
| 2007/0124088 | A1 | 5/2007 | Woo et al. |
| 2007/0129899 | A1 | 6/2007 | Ward et al. |
| 2007/0143070 | A1 | 6/2007 | Kurnik et al. |
| 2007/0148632 | A1 | 6/2007 | Kurnik et al. |
| 2007/0214133 | A1 | 9/2007 | Liberty et al. |
| 2008/0167837 | A1 | 7/2008 | Basak et al. |
| 2008/0234977 | A1 | 9/2008 | Aggarwal et al. |
| 2009/0119020 | A1 | 5/2009 | Kurnik et al. |
| 2009/0192754 | A1 | 7/2009 | Balog et al. |
| 2011/0054852 | A1 | 3/2011 | Titz et al. |

FOREIGN PATENT DOCUMENTS

| | | |
|---|---|---|
| WO | WO/01/31579 | 5/2001 |
| WO | WO/03/029924 | 4/2003 |
| WO | WO/2006/023744 | 3/2006 |
| WO | WO/2007/113622 | 10/2007 |
| WO | WO/2008/039918 | 4/2008 |
| WO | 2011030186 A1 | 3/2011 |
| WO | 2011061568 A1 | 5/2011 |

OTHER PUBLICATIONS

Shieh et al. Statistical Applications in Genetics and Molecular Biology, 2009, vol. 8, Iss. 1, Art. 1, p. 1-26.*
International Search Report and Written Opinion dated Sep. 26, 2012 in corresponding International Application No. PCT/IB2012/052030.
Almeida et al., Improving hierarchical cluster analysis: A new method with outlier detection and automatic clustering. Chemom Intell Lab Syst,2007; 87:208-217.
Brechtbuehl et al., A rapid real-time quantitative polymerase chain reaction for hepatitis B virus. J Virol Methods. Apr. 2001;93(1-2):105-113.
Brereton, Applied Chemometrics for Scientists. John Wiley and Sons LTD, UK, Copyright 2007, pp. 1-397.
Brito et al., Connectivity of the mutual k-nearest-neighbor graph in clustering and outlier detection. Statistics and Probability Letters Aug. 15, 1997;35(1):33-42.
Bylesjo et al., OPLS discriminant analysis: combining the strengths of PLS-DA and SIMCA classification. J Chemom, Aug.-Oct. 2006;20(8-10):341-351.
Chiang and Hao, A New Kernel-Based Fuzzy Clustering Approach: Support Vector Clustering With Cell Growing. IEEE Transactions on Fuzzy Systems. Aug. 2003;11(4):518-527.
Coifman and Lafon, Diffusion maps. Appl Comput Harmon Anal. Jun. 2006; 21:5-30.
Cui and Yan, Adaptive weighted least square support vector machine regression integrated with outlier detection and its application in QSAR. Chemom Intell Lab Syst, 2009;98:130-135.
Fernandez Pierna et. al., Methods for outlier detection in prediction. Chemom Intell Lab Syst, 2002;63(1):27-39.
Filzmoser et al., Multivariate outlier detection in exploration geochemistry. Comp Geosci. 2005;31(5):579-587.
Liu et. al., On-line outlier detection and data cleaning. Comp Chem Engineer. 2004;28(9):1635-1647.
Pell, Multiple outlier detection for multivariate calibration using robust statistical techniques. Chemom Intell Lab Syst, 2000;52(1):87-104.
Riu and Bro, Jack-knife technique for outlier detection and estimation of standard errors in PARAFAC models. Chemom Intell Lab Syst, 2003;65(1):35-49.
Tax et. al., Support vector domain description. Pattern Recogn Lett, Nov. 1999;20(11-13):1191-1199.
Wisnowski et al., A Comparative analysis of multiple outlier detection procedures in the linear regression model. Computational Statistics & Data Analysis. 2001;36(3):351-382.
Worden and Manson, Damage Detection Using Outlier Analysis. J Sound Vibration. Jan. 20, 2000;229(3):647-667.

* cited by examiner

*Primary Examiner* — Michael Borin
(74) *Attorney, Agent, or Firm* — Michael A. Whittaker; Acuity Law Group, P.C.

(57) ABSTRACT

An apparatus for identifying outliers among chemical reaction assays, the apparatus comprising a transition point finder, configured to find at least one transition point in a cumulative function, the cumulative function giving a quantitative indication based on a count of points in a calculated space as a function of distance from a function dividing the calculated space into at least two groups, each one of the points representing results of a respective assay of a chemical reaction. The apparatus further comprises an outlier identifier, in communication with the transition point finder, configured to use a distance of the found transition point from the function dividing the calculated space, as a threshold, for identifying an outlier among the chemical reaction assays.

26 Claims, 14 Drawing Sheets

IDENTIFYING OUTLIERS AMONG CHEMICAL ASSAYS

FIELD AND BACKGROUND OF THE INVENTION

The present invention relates to analyzing chemical reactions and, more particularly, but not exclusively to systems and methods for automatically identifying outliers among chemical reaction assays.

An outlier may be indicative of a measurement error, a contaminated sample, a human error, an experimental error, etc, as known in the art.

Traditionally, the classification of chemical assays is based on manual examination by an expert in the field.

The expert manually examines hundreds or thousands of samples, say thousands of graphs derived from results of Quantitative Fluorescent Polymerase Chain Reaction (QF-PCR) based assays, or other chemical assays.

The expert detects certain features in the samples, and classifies each sample into one of two or more groups.

Typically, the results of the chemical assays are obtained through real time photometric measurements of reactions such as real-time Polymerase Chain Reaction (PCR) and Quantitative Fluorescent Polymerase Chain Reaction (QF-PCR), thus producing a time series of values.

The values produced through the measurements, may be represented in a two dimensional graph depicting spectral changes over time, say of a real-time PCR based assay.

The values may also be represented in a three dimensional graph depicting spectral changes vs. molecule length vs. time, say of a Capillary PCR based assay, etc., as known in the art.

For example, the spectral changes may include Fluorescence Intensity (FI) values measured over a PCR reaction apparatus, as known in the art. The measured FI values are indicative of presence and quantity of specific molecules, as detected in the PCR reaction.

The values measured may be used, to classify the chemical reaction assay into a certain type, to determine if the assay is positive or negative (say with respect to occurrence of a certain genetic mutation), etc.

For example, in QF-PCR, a graph representing the values measured over time may have linear properties, which indicate that no amplification takes place in a reaction apparatus.

Alternatively, the QF-PCR graph may include a sigmoid curve interval, which indicates the occurrence of a DNA amplification reaction in the reaction apparatus.

Parameters extracted from the graph are used to determine the properties of the amplification.

The right combination of parameters, say slopes of the graph in selected points on the graph, may indicate the existence of a specific subject (say the existence of a specific bacterial DNA sequence).

The traditional methods rely on a model built manually, by the expert.

In order to build the model, the expert has to manually examine hundreds or thousands of samples of a training set.

The expert may position points in a coordinate system, say on a paper or on a computer screen. Each of the points represents one the samples. The position of each of the points depends on the parameters extracted from the graph, and represents the results of a respective assay (i.e. a single one of the samples).

Then, the expert classifies each of the samples (as represented by points) into one of two or more groups.

Finally, the expert manually draws a line defining a separation between the two or more groups. For example, the expert may draw a line defining a separation between positive and negative samples.

A new sample may thus be classified into one of the groups based on position of a point which represents the future sample, on one or other side of the line which defines the separation between the groups.

Occasionally, while building the training set, the expert may find some of the samples problematic and difficult to classify into one of the groups, thus finding the problematic samples as outliers.

Some currently used methods are based on automatic classification of samples. For example, some of the currently used methods use SVM (Support Vector Machine), to identify patterns in biological systems.

Support Vector Machines (SVMs) are a set of related supervised learning methods that analyze data and recognize patterns. Supervised learning methods are widely used for classification and regression analysis.

Standard SVM may take a set of input data, and predict for each given input, which of two possible categories the input is a member of.

Given a set of training samples, each marked as belonging to one of the two categories, an SVM training algorithm builds a model usable for assigning a new sample into one category or the other.

Intuitively, the SVM built model is a representation of the samples as points in space, mapped so that the examples of the separate categories are divided by a clear gap.

Consequently, new samples may be mapped into that same space and predicted to belong to one of the categories, based on which side of the gap the new samples fall on.

SUMMARY OF THE INVENTION

According to one aspect of the present invention there is provided an apparatus for identifying outliers among chemical reaction assays, the apparatus comprising: a transition point finder, configured to find at least one transition point in a cumulative function, the cumulative function giving a quantitative indication based on a count of points in a calculated space as a function of distance from a function dividing the calculated space into at least two groups, each one of the points representing results of a respective assay of a chemical reaction, and an outlier identifier, in communication with the transition point finder, configured to use a distance of the found transition point from the function dividing the calculated space, as a threshold, for identifying an outlier among the chemical reaction assays.

According to a second aspect of the present invention there is provided a computer implemented method for identifying outliers among chemical reaction assays, the method comprising steps the computer is programmed to perform, the steps comprising: finding at least one transition point in a cumulative function, the cumulative function giving a quantitative indication based on a count of points in a calculated space as a function of distance from a function dividing the calculated space into at least two groups, each one of the points representing results of a respective assay of a chemical reaction, and using a distance of the found transition point from the function dividing the calculated space, as a threshold, for identifying an outlier among the chemical reaction assays.

According to a third aspect of the present invention there is provided a computer readable medium storing computer executable instructions for performing steps of identifying outliers among chemical reaction assays, the steps comprising: finding at least one transition point in a cumulative function, the cumulative function giving a quantitative indication based on a count of points in a calculated space as a function of distance from a function dividing the calculated space into at least two groups, each one of the points representing results of a respective assay of a chemical reaction, and using a distance of the found transition point from the function dividing the calculated space, as a threshold, for identifying an outlier among the chemical reaction assays.

Unless otherwise defined, all technical and scientific terms used herein have the same meaning as commonly understood by one of ordinary skill in the art to which this invention belongs. The materials, methods, and examples provided herein are illustrative only and not intended to be limiting.

Implementation of the method and system of the present invention involves performing or completing certain selected tasks or steps manually, automatically, or a combination thereof.

Moreover, according to actual instrumentation and equipment of preferred embodiments of the method and system of the present invention, several selected steps could be implemented by hardware or by software on any operating system of any firmware or a combination thereof.

For example, as hardware, selected steps of the invention could be implemented as a chip or a circuit. As software, selected steps of the invention could be implemented as a plurality of software instructions being executed by a computer using any suitable operating system. In any case, selected steps of the method and system of the invention could be described as being performed by a data processor, such as a computing platform for executing a plurality of instructions.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in order to provide what is believed to be the most useful and readily understood description of the principles and conceptual aspects of the invention. The description taken with the drawings making apparent to those skilled in the art how the several forms of the invention may be embodied in practice.

In the drawings.

DESCRIPTION OF THE PREFERRED EMBODIMENTS

Figure 1:
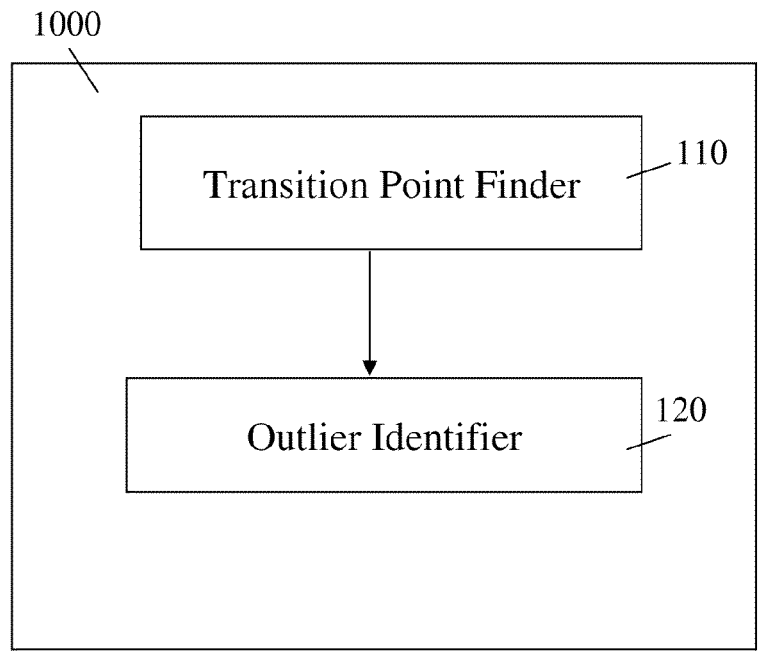
FIG. 1 is a block diagram schematically illustrating a first apparatus for identifying outliers among chemical reaction assays, according to an exemplary embodiment of the present invention.

The present embodiments comprise an apparatus, a computer readable medium, and a method, for automatically identifying outliers among chemical reaction assays.

In a method according to exemplary embodiments of the present invention, results of chemical reaction assays are represented as points in a mathematical space, as described in further detail hereinbelow.

The space is calculated using the results, such that each of the points represents a respective one of the chemical reaction assays.

The points are divided into two or more groups, using a function which divides the calculated space into the groups, say a function which defines a line or a hyper-surface which divides the space into two groups, as described in further detail hereinbelow.

Optionally, the function, which divides the calculated space, is resultant upon SVM (Support Vector Machine) classification of the points, as described in further detail hereinbelow.

In the method, there is calculated a cumulative function.

The cumulative function gives a quantitative indication based on a count of points in the calculated space as a function of distance from the function which divides the calculated space into the groups.

In one example, the cumulative function gives the number of points within a distance from the function which divides the calculated space into the groups.

When the calculated space includes points which concentrate in groups, the cumulative function has a sigmoid form, and is thus characterized by transition points also referred to hereinbelow, as elbow points.

Next, the cumulative function searched for a transition point (i.e. an elbow point).

A transition point is point in which the cumulative function's slope changes significantly.

For example, the transition point may be a point in which a change in the cumulative function's slope is maximal (typically, a point in which the cumulative function second derivative's absolute value is maximal), a point in which the cumulative function shifts from a relatively linear slope to a significantly exponential slope (or vise versa), etc., as described in further detail hereinbelow.

Finally, a distance of the found transition point from the function which divides the calculated space is used as a threshold, for identifying an outlier among the chemical reaction assays.

That is to say that points residing within a distance smaller than the distance of the transition point from the function which divides the calculated space, are found to be outliers.

Outliers are points that though falling in one of the groups, lack a strong enough linkage to the group, and are characterized by excessive proximity to the function which divides the calculated space into the groups.

Consequently, assays represented by the points found to be outliers, may be classified as erroneous.

Optionally, the outliers are indicative of a measurement error, a contaminated sample, a human error, an experimental error, etc, as known in the art.

In one example, an outlier is a point which represents results of a Polymerase Chain Reaction (PCR) based assay, mistakenly classified into a group of positive assays, although no significant amplification occurs in the assay.

In another example, an outlier is a point which represents a PCR based assay, mistakenly classified into a group of negative assays though exponential amplification does occur in the PCR based assay.

The principles and operation of an apparatus according to the present invention may be better understood with reference to the drawings and accompanying description.

Before explaining at least one embodiment of the invention in detail, it is to be understood that the invention is not limited in its application to the details of construction and the arrangement of the components set forth in the following description or illustrated in the drawings.

The invention is capable of other embodiments or of being practiced or carried out in various ways. Also, it is to be understood that the phraseology and terminology employed herein is for the purpose of description and should not be regarded as limiting.

Reference is now made to FIG. 1, which is a block diagram schematically illustrating a first apparatus for identifying outliers among chemical reaction assays, according to an exemplary embodiment of the present invention.

Apparatus 1000 may be implemented as a computer program, as hardware, as a combination of a computer program and hardware, etc.

The apparatus 1000 may be implemented as a computer server application in remote communication with one or more dedicated client programs installed on remote user computers, say in a Software-as-a-Service (SaaS) mode, as known in the art.

Apparatus 1000 may also be implemented as a computer program installed on a user's computer (say a desktop computer, a laptop computer, a tablet computer, a cellular phone, etc).

Apparatus 1000 includes a transition point finder 110.

The transition point finder 110 finds one or more transition points in a cumulative function, as described in further detail hereinbelow.

The cumulative function (say a mathematical function) gives a quantitative indication based on a count of points in a calculated space, as a function of distance from a function which divides the calculated space into two (or more) groups, as described in further detail hereinbelow.

Each one of the points represents results of a respective assay of a chemical reaction.

Optionally, the quantitative indication is the number of points in the calculated space as a function of the distance from the function which divides the calculated space into the groups.

Optionally, the distance is a conventional analytic geometry distance, which is the shortest distance between the point and the function (i.e. a normal), as known in the art.

Optionally, the distance is a rectilinear distance, as known in the art.

Optionally, the quantitative indication is a density of points (say a number of points per one unit of space) in the calculated space, as a function of the distance from the function which divides the calculated space.

Optionally, the cumulative function is specific to one of the groups, as described in further detail hereinbelow.

Optionally, the cumulative function is common to two or more of the groups, as described in further detail hereinbelow.

Optionally, the function which divides the calculated space, defines one or more lines, as described in further detail hereinbelow.

Optionally, the function which divides the calculated space, defines one or more hyper-surfaces, as described in further detail hereinbelow.

Optionally, the function which divides the space is a polynomial function.

Optionally, the calculated space is a space which enhances proximity among points that represent assays of qualitatively identical chemical reactions, such as a space calculated using diffusion mapping or another dimensionality reduction technique, as described in further detail hereinbelow.

The apparatus 1000 further includes an outlier identifier 120, in communication with the transition point finder 110.

The outlier identifier 120 uses a distance of the found transition point from the function which divides the calculated space, as a threshold, for identifying an outlier among the chemical reaction assays, as described in further detail hereinbelow.

Optionally, the apparatus 1000 further includes a cumulative function calculator, which calculates the cumulative function, as described in further detail hereinbelow.

Optionally, the apparatus 1000 further includes a result receiver, which receives a plurality of sets of results, each one of the received sets of results pertaining to a respective assay of a chemical reaction.

Optionally, the apparatus 1000 further includes a space calculator, which calculates the space, using the received sets of results, as described in further detail hereinbelow.

Optionally, the space calculator calculates the space, using dimensionality reduction.

For example, the space calculator may calculate the space using diffusion mapping or another dimensionality reduction technique, as described in further detail hereinbelow.

Optionally, the apparatus 1000 further includes a dividing function calculator, which calculates the function which divides the calculated space, say using a Support Vector Machine (SVM), as described in further detail hereinbelow.

Optionally, the apparatus 1000, further includes an out-of-sample classifier, which classifies results of a new assay not represented in the space as originally calculated, using out-of-sample extension, as described in further detail hereinbelow.

Figure 2:
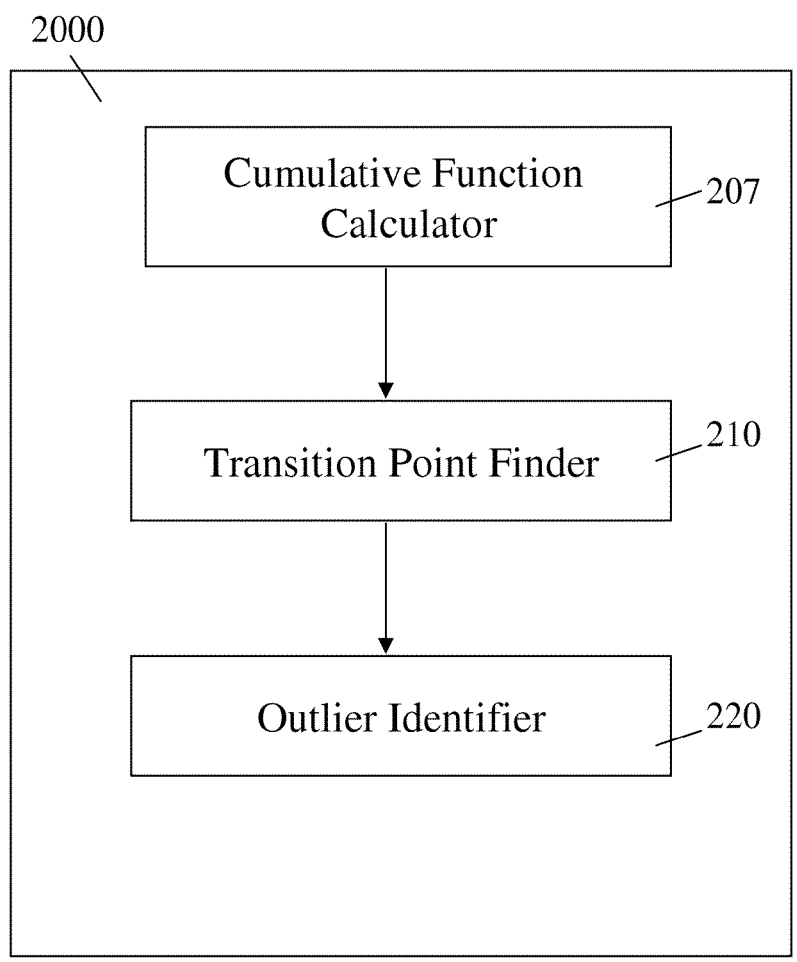
FIG. 2 is a block diagram schematically illustrating a second apparatus for identifying outliers among chemical reaction assays, according to an exemplary embodiment of the present invention.

Reference is now made to FIG. 2, which is a block diagram schematically illustrating a second apparatus for identifying outliers among chemical reaction assays, according to an exemplary embodiment of the present invention.

Apparatus 2000 may be implemented as a computer program, as hardware, as a combination of a computer program and hardware, etc.

The apparatus 2000 may be implemented as a computer server application in remote communication with one or more dedicated client programs installed on remote user computers, say in a Software-as-a-Service (SaaS) mode, as known in the art.

Apparatus 2000 may also be implemented as a computer program installed on a user's computer (say a desktop computer, a laptop computer, a tablet computer, a cellular phone, etc).

Apparatus 2000 includes a cumulative function calculator 207.

The cumulative function calculator 207 calculates a cumulative function, as described in further detail hereinbelow.

The cumulative function (say a mathematical function) gives a quantitative indication based on a count of points in a calculated space, as a function of distance from a function which divides the calculated space into two (or more) groups, as described in further detail hereinbelow.

Optionally, the distance is a conventional analytic geometry distance, which is the shortest distance between the point and the function (i.e. a normal), as known in the art.

Optionally, the distance is a rectilinear distance, as known in the art.

Each one of the points represents results of a respective assay of a chemical reaction.

Optionally, the quantitative indication is the number of points in the calculated space as a function of the distance from the function which divides the calculated space.

Optionally, the quantitative indication is a density of points in the calculated space as a function of the distance from the function which divides the calculated space, say a number of points per one unit of space, as described in further detail hereinbelow.

Optionally, the cumulative function is specific to one of the groups, as described in further detail hereinbelow.

Optionally, the cumulative function is common to two or more of the groups, as described in further detail hereinbelow.

Apparatus 2000 further includes a transition point finder 210, in communication with the cumulative function calculator 207.

The transition point finder 210 finds one or more transition points in the cumulative function calculated by the cumulative function calculator 207, as described in further detail hereinbelow.

Optionally, the function which divides the calculated space, defines one or more lines, as described in further detail hereinbelow.

Optionally, the function which divides the calculated space, defines one or more hyper-surfaces, as described in further detail hereinbelow.

Optionally, the function which divides the space is a polynomial function.

Optionally, the calculated space is a space which enhances proximity among points that represent assays of qualitatively identical chemical reactions, such as a space calculated using diffusion mapping, or another dimensionality reduction technique, as described in further detail hereinbelow.

The apparatus 2000 further includes an outlier identifier 220, in communication with the transition point finder 210.

The outlier identifier 220 uses a distance of the found transition point from the function which divides the calculated space, as a threshold, for identifying one or more outliers among the chemical reaction assays, as described in further detail hereinbelow.

Optionally, the apparatus 2000 further includes a result receiver, which receives a plurality of sets of results, each one of the received sets of results pertaining to a respective assay of a chemical reaction.

Optionally, the apparatus 2000 further includes a space calculator, which calculates the space, using the received sets of results, as described in further detail hereinbelow.

Optionally, the space calculator calculates the space, using dimensionality reduction.

For example, the space calculator may calculate the space using diffusion mapping or another dimensionality reduction technique, as described in further detail hereinbelow.

Optionally, the apparatus 2000 further includes a dividing function calculator, which calculates the function which divides the calculated space, say using a Support Vector Machine (SVM), as described in further detail hereinbelow.

Optionally, the apparatus 2000, further includes an out-of-sample classifier, which classifies results of a new assay not represented in the space as originally calculated, using out-of-sample extension, as described in further detail hereinbelow.

Figure 3:
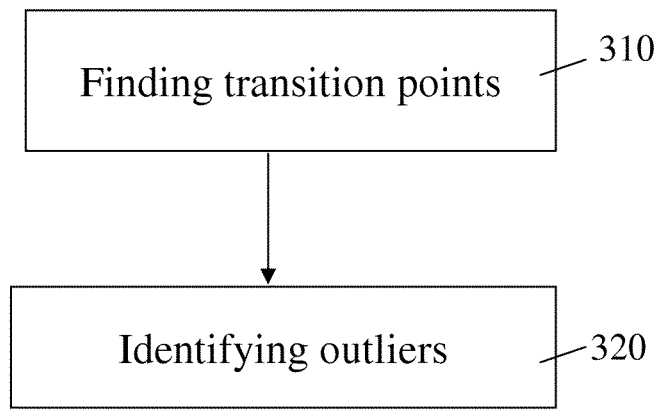
FIG. 3 is a simplified flowchart schematically illustrating a first method for identifying outliers among chemical reaction assays, according to an exemplary embodiment of the present invention.

Reference is now made to FIG. 3 which is a simplified flowchart schematically illustrating a first method for identifying outliers among chemical reaction assays, according to an exemplary embodiment of the present invention.

A first exemplary method, according to an exemplary embodiment of the present invention, may be implemented on a computer, say using a computer server application in remote communication with one or more dedicated client programs installed on remote user computers, say in a Software-as-a-Service (SaaS) mode, as known in the art.

The first exemplary method may also be implemented using a computer program installed on a user's computer (say a desktop computer, a laptop computer, a tablet computer, a cellular phone, etc).

In the first exemplary method, there are found 310 one or more transition points in a cumulative function, say using the transition point finder 110 of the exemplary apparatus 1000, as described in further detail hereinbelow.

The cumulative function (say a mathematical function) gives a quantitative indication based on a count of points in a calculated space, as a function of distance from a function which divides the calculated space into two (or more) groups.

Optionally, the distance is a conventional analytic geometry distance, which is the shortest distance between the point and the function (i.e. a normal), as known in the art.

Optionally, the distance is a rectilinear distance, as known in the art.

Each one of the points represents results of a respective assay of a chemical reaction.

Optionally, the quantitative indication is a number of points in the calculated space as a function of the distance from the function which divides the calculated space.

Optionally, the quantitative indication is a density of points in the calculated space as a function of the distance from the function which divides the calculated space, say a number of points per one unit of space, as described in further detail hereinbelow.

Optionally, the cumulative function is specific to one of the groups, as described in further detail hereinbelow.

Optionally, the cumulative function is common to two or more of the groups, as described in further detail hereinbelow.

Optionally, the function which divides the calculated space, defines one or more lines, as described in further detail hereinbelow.

Optionally, the function which divides the calculated space, defines one or more hyper-surfaces, as described in further detail hereinbelow.

Optionally, the function which divides the space is a polynomial function.

Optionally, the calculated space is a space which enhances proximity among points that represent assays of qualitatively identical chemical reactions, such as a space calculated using diffusion mapping or another dimensionality reduction technique, as described in further detail hereinbelow.

Next, there is used a distance of the found transition point from the function which divides the calculated space, as a threshold, for identifying 320 outliers among the chemical reaction assays, as described in further detail hereinbelow.

Optionally, the first exemplary method further includes calculating the cumulative function, as described in further detail hereinbelow.

Optionally, the first exemplary method further includes receiving a plurality of sets of results, each one of the received sets of results pertaining to a respective assay of a chemical reaction.

Optionally, the first exemplary method further includes calculating the space, using the received sets of results, as described in further detail hereinbelow.

Optionally, the space is calculated using dimensionality reduction.

For example, the first exemplary method may include calculating the space, using diffusion mapping or another dimensionality reducing technique, as described in further detail hereinbelow.

Optionally, the first exemplary method further includes calculating the function which divides the calculated space, say using a Support Vector Machine (SVM), as described in further detail hereinbelow.

Optionally, the first exemplary method further includes classifying results of a new assay not represented in the space as originally calculated, using out-of-sample extension, as described in further detail hereinbelow.

Figure 4:
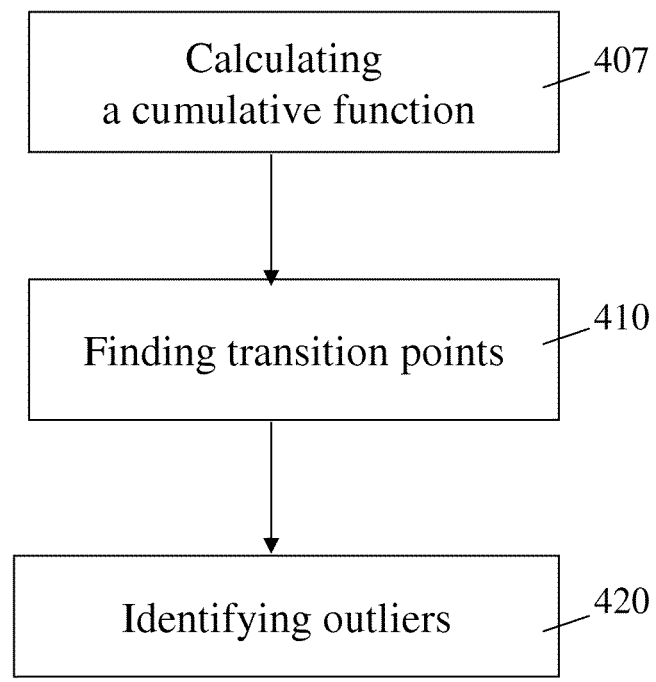
FIG. 4 is a simplified flowchart schematically illustrating a second method for identifying outliers among chemical reaction assays, according to an exemplary embodiment of the present invention.

Reference is now made to FIG. 4 which is a simplified flowchart schematically illustrating a second method for identifying outliers among chemical reaction assays, according to an exemplary embodiment of the present invention.

A second exemplary method, according to an exemplary embodiment of the present invention, may be implemented on a computer, say using a computer server application in remote communication with one or more dedicated client programs installed on remote user computers, say in a Software-as-a-Service (SaaS) mode, as known in the art.

The second exemplary method may also be implemented using a computer program installed on a user's computer (say a desktop computer, a laptop computer, a tablet computer, a cellular phone, etc).

In the second exemplary method, there is calculated 407 a cumulative function, as described in further detail hereinbelow.

The cumulative function (say a mathematical function) gives a quantitative indication based on a count of points in a calculated space as a function of distance from a function which divides the calculated space into two (or more) groups.

Optionally, the distance is a conventional analytic geometry distance, which is the shortest distance between the point and the function, say a normal, as known in the art.

Optionally, the distance is a rectilinear distance, as known in the art.

Each one of the points represents results of a respective assay of a chemical reaction.

Optionally, the quantitative indication is a number of points in the calculated space as a function of the distance from the function which divides the calculated space.

Optionally, the quantitative indication is a density of points in the calculated space as a function of the distance from the function which divides the calculated space, say a number of points per one unit of space.

Optionally, the cumulative function is specific to one of the groups, as described in further detail hereinbelow.

Optionally, the cumulative function is common to two or more of the groups, as described in further detail hereinbelow.

Optionally, the function which divides the calculated space, defines one or more lines, as described in further detail hereinbelow.

Optionally, the function which divides the calculated space, defines one or more hyper-surfaces, as described in further detail hereinbelow.

Optionally, the function which divides the space is a polynomial function.

Optionally, the calculated space is a space which enhances proximity among points that represent assays of qualitatively identical chemical reactions, such as a space calculated using diffusion mapping or another dimensionality reduction technique, as described in further detail hereinbelow.

Next, there are found 410 one or more transition points in a cumulative function, say using the transition point finder 210 of the exemplary apparatus 2000, as described in further detail hereinbelow.

Finally, there is used a distance of the found transition point from the function which divides the calculated space, as a threshold, for identifying 420 outliers among the chemical reaction assays, as described in further detail hereinbelow.

Optionally, the second exemplary method further includes receiving a plurality of sets of results, each one of the received sets of results pertaining to a respective assay of a chemical reaction.

Optionally, the second exemplary method further includes calculating the space, using the received sets of results, as described in further detail hereinbelow.

Optionally, the space is calculated using dimensionality reduction.

For example, the second exemplary method may include calculating the space, using diffusion mapping or another dimensionality reducing technique, as described in further detail hereinbelow.

Optionally, the second exemplary method further includes calculating the function which divides the calculated space, say using a Support Vector Machine (SVM), as described in further detail hereinbelow.

Optionally, the second exemplary method further includes classifying results of an assay not represented in the space as originally calculated, using out-of-sample extension, as described in further detail hereinbelow.

Figure 5:
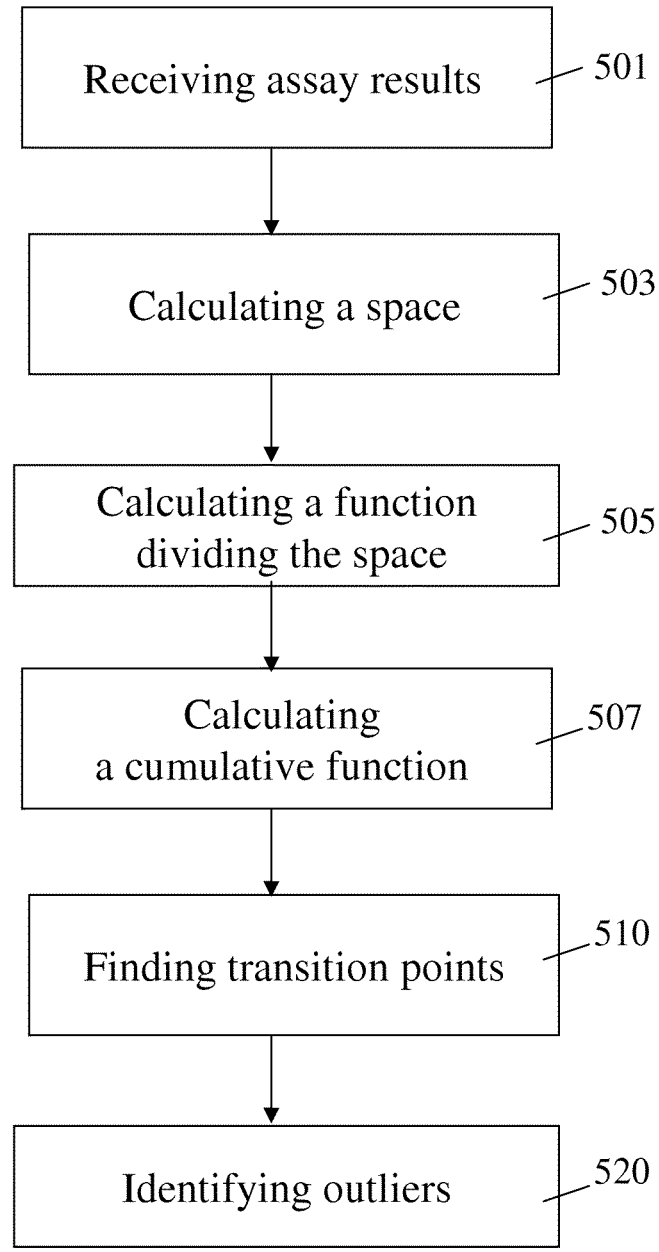
FIG. 5 is a simplified flowchart schematically illustrating a third method for identifying outliers among chemical reaction assays, according to an exemplary embodiment of the present invention.

Reference is now made to FIG. 5, which is a simplified flowchart schematically illustrating a third method for identifying outliers among chemical reaction assays, according to an exemplary embodiment of the present invention.

A third exemplary method, according to an exemplary embodiment of the present invention, may be implemented on a computer, say using a computer server application in remote communication with one or more dedicated client programs installed on remote user computers, say in a Software-as-a-Service (SaaS) mode, as known in the art.

The third exemplary method may also be implemented using a computer program installed on a user's computer (say a desktop computer, a laptop computer, a tablet computer, a cellular phone, etc).

In the third exemplary method, there are received 501 sets of results. Each one of the received sets of results pertains to a respective assay of a chemical reaction.

The sets of results may be received 501 as variables.

The variables may hold measurement values, such as: Fluorescence Intensity (FI) values of elbow points of a sigmoid graph depicting the assay of the chemical reaction, time of each of the elbow points, FI values of certain points of the graph, pH values measured during or after the reaction, amounts of products yielded in the reaction, etc.

Then, there is calculated 503 a mathematical space in which each one of the chemical reaction assays is represented by a respective point. The point is positioned in the calculated 503 space according to the assay's set of results (as in the received 501 variables).

Optionally, the calculated 503 space is a Euclidean space dimensioned according to variables' number in each set of assay results. Each of the points is positioned in the calculated 503 space, such that each coordinate value of the point corresponds to one of the variables received 501 for the assay represented by the point.

Optionally, the calculated 503 space is a space which enhances proximity among points that represent assays of qualitatively identical chemical reactions, as described in further detail hereinbelow.

Methods which may be used for calculating 503 the space, may further include, but are not limited to: Dimensionality Reduction methods such as Diffusion Mapping, as well as Kernel Principal Component Analysis (Kernel PCA) methods.

Dimensionality Reduction also referred to as Manifold Learning, is a process of reducing the number of variables under consideration. Dimensionality Reduction may be divided into Feature Selection and Feature Extraction.

Feature Selection, also known as Variable Selection, Feature Reduction, Attribute Selection or Variable Subset Selection, is a technique, commonly used in machine learning.

With Feature Selection, there is selected a subset of relevant features, for building robust learning models, as known in the art.

In Feature Extraction, when data input to an algorithm is too large to be processed and is suspected to be redundant, the input data is transformed into a representation based on a reduced number of features (also named a feature vector), as known in the art.

If the features extracted are carefully selected, it is expected that the selected features include only information which is essential for performing a desired task (say, for dividing the assays into the groups), instead of the whole input data.

Although Dimension Reduction is a technique which usually involves narrowing down a space's dimension number, Dimension Reduction may also involve modifying metrics (say strengthening affinity between points of qualitatively identical assays), without reducing the number of dimensions.

Examples of dimension reduction techniques include, but are not limited to: Diffusion Mapping, Anisotropic Mapping, Multi Dimensional Scaling (MDS), Local Linear Embedding (LLE) and Local Multi Dimensional Scaling (Local MDS), as known in the art.

Diffusion Mapping is a recently developed method of dimensionally reduction, which belongs to a method group known as Kernel Principal Component Analysis (Kernel PCA).

For example, Ronald R. Coifman and Stephane Lafon describe Diffusion Mapping in an article entitled "Diffusion Maps", published in Applied and Computational Harmonic Analysis: Special issue on Diffusion Maps and Wavelets, Vol 21, July 2006, pp 5-30.

Coifman and Lafon show in the article, among other things, that the Diffusion Distance (as defined in the article) in a Euclidean space equals the Euclidean distance (as defined in the article) in a corresponding Diffusion Space.

Diffusion mapping automatically differentiates variable groups in data (such as the sets of results described hereinabove), according to how clustered they are.

Diffusion mapping further extracts minimal sets of meaningful variables. The minimal sets describe the input data. All results are taken into account for the extraction. The differentiation is based on geometrical separation between the results, as described in further detail hereinbelow.

Optionally, the sets of results are first represented in a Euclidean space dimensioned according to variables' number in each set of results, as illustrated using FIG. 7 hereinbelow.

Then, by applying diffusion mapping on the Euclidian space, there is calculated 503 a space in which the distance between any two of the points depends on a number of short paths between the two points, as found in the Euclidean space.

Short paths connect the two points through a number of points.

Each of the points in the short path may be directly connected only to a point in the connected point's vicinity.

The distance between the points further depends on the lengths of the short paths. The lower is the number of the points connected in the short path, the higher is the weight of the short path, and the closer are the points.

That is to say that the space calculated 503 using diffusion mapping, enhances proximity among points that represent assays of qualitatively identical chemical reactions.

The space calculated 503 using diffusion mapping, further provides for easier recognition of grouping among the points, based on highest-density areas of the calculated 503 space, as illustrated using FIG. 8 hereinbelow.

Next, there is calculated 505 a function which divides the calculated 503 space into two or more groups.

Optionally, the function which divides the space may be calculated 505 using one or more of currently known classification methods, such as simple Nearest-Neighbor methods, K-Means, Fuzzy K-Means, C-Means, Neuronal Networks, SVM (Support Vector Machine), etc.

The calculation 505 of the function may also be based on a manual or semi-manual process, in which the points in the space are presented graphically to a user, on a computer screen, and the user is allowed to draw one or more lines which divide the space into the two or more groups.

In one example, the function which divides the space is calculated 505 using a SVM (Support Vector Machine).

Support Vector Machines (SVMs) are a set of related supervised learning methods that analyze data and recognize patterns. SVM is widely used for classification and regression analysis, as known in the art.

A Standard SVM may take a set of input data and predict, for each given input data, which one of possible categories the input data belongs to.

Given a set of training examples, each marked as belonging to one of the categories, a SVM training algorithm builds a model usable for assigning a new example into one of the categories.

Intuitively, a model built by SVM, is a representation of the examples as points in a space, mapped so that the examples of the separate categories are divided by a clear gap.

Consequently, a new example may be mapped into the same space and be predicted to belong to one of the categories, based on which side of the gap the new example falls on.

In one example, the SVM is used to divide the space into two groups: one negative and one positive, using points that represent known positive and known negative assays (i.e. control samples), while ignoring points that represent other assays, in the calculated 503 space.

In the example, there is used a standard SVM, to classify the points, by calculating 505 the function which divides the calculated 503 space into the two categories of points (negative assays and positive assays), based on the assays known as negative or positive (i.e. control samples).

The standard SVM used may involve a polynomial discriminant function, with a soft margin, as known in the art. That is to say that the standard SVM used may tolerate a small number of erroneous control samples. An erroneous control sample is a sample marked as positive, which falls negative in the example, or vise versa.

Optionally, the calculated 505 function which divides the calculated 503 space is a polynomial function.

In one example, the calculated 503 space is bi-dimensional and the calculated 505 function defines a line, which divides the calculated 503 space into two groups, as illustrated using FIG. 9A, hereinbelow.

In other examples, the calculated 505 function may divide the calculated 503 space into three or more groups (say a function which defines two separate lines, as illustrated using FIG. 9B hereinbelow).

Optionally, the calculated 503 space is rather three-dimensional, and the calculated 505 function defines one or more bi-dimensional hyper-surfaces, as illustrated using FIG. 9C, hereinbelow.

The discriminant function's sign at any of the points in the calculated 503 space gives the classification of the point as positive or negative.

That is to say that once the SVM calculates 505 the function dividing the space (using the control samples), all points in the calculated 503 space may be classified as negative or positive, using the discriminant function.

In one example, the discriminant function's value at the point gives the confidence level at the point. The discriminant function value is a function of the distance of the point from the calculated 505 function (i.e. from the line or hyper-surface which divides the space into the positive and negative groups). Optionally, the confidence value equals or roughly corresponds to the distance from the calculated 505 function, or to a value resultant upon normalization of the distance, as known in the art.

Next, there is calculated 507 a cumulative function, as illustrated using FIG. 11, hereinbelow.

The cumulative function (say a mathematical function) gives a quantitative indication based on a count of points in the calculated 503 space, as a function of distance from the calculated 505 function which divides the calculated 503 space into the two groups.

Optionally, the quantitative indication is a number of points in the calculated 503 space as a function of the distance from the function which divides the calculated 503 space.

Optionally, the distance is a conventional analytic geometry distance, which is the shortest distance between the point and the function, say a normal, as known in the art.

Optionally, the distance is a rectilinear distance, as known in the art.

In one example, the cumulative function is denoted $F_{(X)}$.

Optionally, $F_{(X)}$ indicates how many of the points have a confidence value between 0 and x, as given by the SVM discriminant function's absolute value at points on either of side of the function which divides the calculated 503 space. In the example, x is equal to the distance from the calculated 505 function which divides the space, or to a value resultant upon normalization of the distance, as known in the art.

Alternatively, the cumulative function of the example may be denoted $F_{(X-D)}$ and indicate how many of the points have a confidence value between x and x-d, as given by the SV discriminant function's absolute value, where d is a number between x and 0, and x is equals to the distance from the function which divides the calculated 503 space, or to a value resultant upon normalization of the distance, as known in the art.

Optionally, the quantitative indication is a density of points in the calculated 503 space (say number of points per one unit of space), as a function of the distance from the calculated 505 function which divides the calculated 503 space.

Optionally, the cumulative function is rather calculated 507 separately for points on one side of the calculated 505 function which divides the calculated 503 space, and for points on the other side of the calculated 505 function, as described in further detail hereinbelow.

Next, there are found 510 transition points (i.e. elbow points) in the cumulative function, as illustrated using FIG. 11, hereinbelow.

When the calculated 503 space includes points which concentrate in groups, the cumulative function has a sigmoid form, with typical transition points, also referred to hereinbelow as elbow points.

For example, the cumulative function denoted $F_{(X)}$ may have a transition point with a specific x value. The x value gives a distance of the transition point from the calculated 505 function which divides the space.

Optionally, the transition points are found 510 using the transition point finder 110 of the exemplary apparatus 1000, as described in further detail hereinabove.

When the cumulative function is calculated 507 separately for each side of the calculated 505 function which divides the space, transition points are found 510 separately for each of the two sides, as described in further detail hereinbelow.

The transition points may be found using a variety of methods including, but not limited to: base-lining operations, Levenberg-Marquardt (LM) regression processes, curvature analysis by comparison with a first or a second degree polynomial curve which fits a growth type of the cumulative function, rotational transformation of a curve defined by the cumulative function, linear regression methods, etc., as known in the art.

In a slope based example, one or more transition points are found 510, by a comparison with a second function.

The second function may be a linear function which connects the edges (i.e. first and last point) of a curve defined by the cumulative function, a linear function with a slope parallel to a slope of the linear function which connects the edges, or a non-linear function with a line of best fit which parallels the slope of the linear function which connects the edges.

In the slope based example, the transition point is found 510 by calculating a difference between the cumulative function and the second function, and identifying one or more extremum points on a graph which represents the calculated difference.

The extremum point indicates a distance of the found 510 transition point from the calculated 505 function which divides the calculated 503 space.

Next, there is used the distance of the transition point found 510 in the cumulative function from the function which divides the calculated space, as a threshold, for identifying 520 outliers among the chemical reaction assays, as described in further detail hereinbelow.

In a first example, the cumulative function is specific to one of the groups.

More specifically, in the first example, the cumulative function is calculated 507 separately for each specific one of the two sides of the space, as divided by the calculated 505 function, say using values of the SVM's polynomial discriminant function, on each point known to belong on the specific side.

That is to say that a first cumulative function is calculated 507 using the points known to represent negative assays, and a second cumulative function is calculated 507 using the points known to represent positive assays.

Consequently, two transition points are found 510 (one among the known negative assays and one among the known positive assays).

In the first example, any point positioned between the two transition points, is found 520 to be an outlier, as described in further detail hereinabove.

In a second example, the cumulative function is common to two or more of the groups.

More specifically, in the second example, the cumulative function is calculated 507 jointly for both sides of the space as divided by the calculated 505 function which divides the space into two groups, say using absolute values of the SVM's polynomial discriminant function, on each point of the control samples (i.e. both the known negative and the known positive assays).

Consequently, only one transition points is found 510.

In the second example, any point positioned within a distance smaller than the distance of the found 510 transition point, from the function which divides the calculated 503 space, is found 520 to be an outlier, as described in further detail hereinabove.

Optionally, the third exemplary method further includes classifying results of a new assay not represented in the space as originally calculated, using out-of-sample extension, as known in the art.

For example, the results of the new assay may be positioned in the calculated 503 space, using an out-of-sample method compatible with the calculated 503 space, as known in the art. Alternatively, the space is re-calculated using the new assay and the results of all assays represented in the space as originally calculated 503, thus positioning all points in the re-calculated space.

Then, the original SVM discriminant function is applied on a point which represents the results of the new assay.

The sign of the discriminant function on the point serves to classify the new assay. The value of the discriminant function on the point gives the confidence level, as described in further detail hereinabove.

The discriminant function value is a function of the distance of the point from the calculated 505 function (i.e. from the line or hyper-surface which divides the space into the positive and negative groups). Optionally, the confidence value equals or roughly corresponds to the distance from the calculated 505 function, as described in further detail hereinabove.

The originally found 510 transition points' distances from the calculated 505 function, are used as threshold values, to determine if the point is an outlier, using the point's confidence level, just as for points represented in the space as originally calculated 503.

Figure 6:
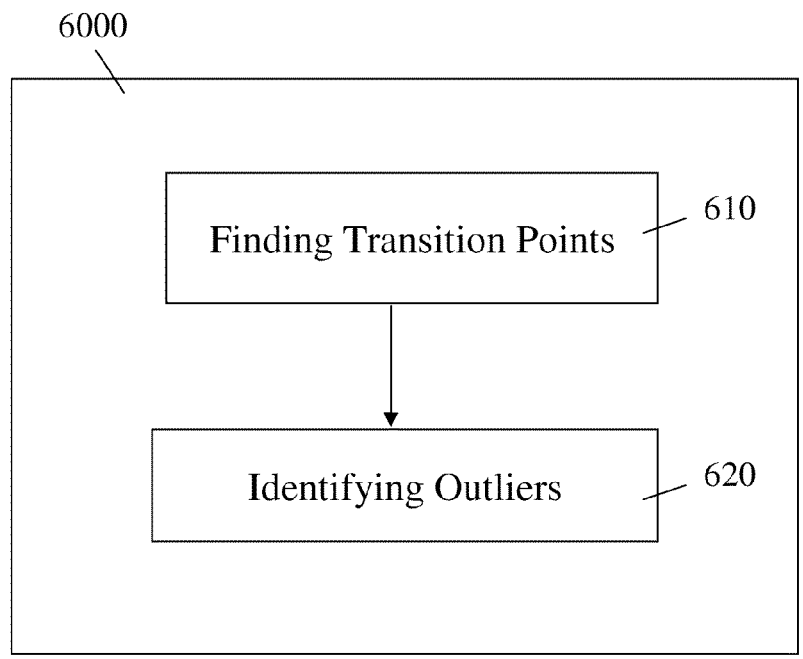
FIG. 6 is a block diagram schematically illustrating a computer readable medium storing computer executable instructions for performing steps of identifying outliers among chemical reaction assays, according to an exemplary embodiment of the present invention.

Reference is now made to FIG. 6, which is a block diagram schematically illustrating a computer readable medium storing computer executable instructions for performing steps of identifying outliers among chemical reaction assays, according to an exemplary embodiment of the present invention.

According to an exemplary embodiment of the present invention, there is provided a computer readable medium 6000, such as a CD-ROM, a USB-Memory, a Portable Hard Disk, a diskette, etc.

The computer readable medium 6000 stores computer executable instructions for performing steps of identifying outliers among chemical reaction assays, according to an exemplary embodiment of the present invention.

The computer executable instructions include a step of finding 610 one or more transition points in a cumulative function, as described in further detail hereinabove.

The cumulative function (say a mathematical function) gives a quantitative indication based on a count of points in a calculated space as a function of distance from a function which divides the calculated space into two (or more) groups, as described in further detail hereinabove.

Each one of the points represents results of a respective assay of a chemical reaction.

Optionally, the distance is a conventional analytic geometry distance, which is the shortest distance between the point and the function, say a normal, as known in the art.

Optionally, the distance is a rectilinear distance, as known in the art.

Optionally, the quantitative indication is a number of points in the calculated space as a function of the distance from the function which divides the calculated space.

Optionally, the quantitative indication is a density of points in the calculated space as a function of the distance from the function which divides the calculated space, say a number of points per one unit of space.

Optionally, the function which divides the calculated space, defines one or more lines, as described in further detail hereinabove.

Optionally, the function which divides the calculated space, defines one or more hyper-surfaces, as described in further detail hereinabove.

Optionally, the function which divides the space is a polynomial function.

Optionally, the calculated space is a space which enhances proximity among points that represent assays of qualitatively identical chemical reactions, such as a space calculated using diffusion mapping or another dimensionality reduction technique, as described in further detail hereinabove.

The computer executable instructions further include a step in which a distance of the found transition point from the function which divides the calculated space, is used as a threshold, for identifying 620 outliers among the chemical reaction assays, as described in further detail hereinabove.

Optionally, the computer executable instructions further include a step of calculating the cumulative function, as described in further detail hereinabove.

Optionally, the computer executable instructions further include a step of receiving a plurality of sets of results. Each one of the received sets of results pertains to a respective assay of a chemical reaction.

Optionally, the computer executable instructions further include a step of calculating the space, using the received sets of results, as described in further detail hereinabove.

Optionally, the space is calculated using dimensionality reduction.

For example, the computer executable instructions may include a step of calculating the space, using diffusion mapping or another dimensionality reducing technique, as described in further detail hereinbelow.

Optionally, the computer executable instructions further include a step of calculating the function which divides the calculated space, say using a Support Vector Machine (SVM), as described in further detail hereinbelow.

Optionally, the computer executable instructions further include a step of classifying results of an assay not represented in the space as originally calculated, using out-of-sample extension, as described in further detail hereinabove.

FIG. 7-12 serve to graphically illustrate a fourth exemplary method for outlier identification, according to an exemplary embodiment of the present invention.

Figure 7:
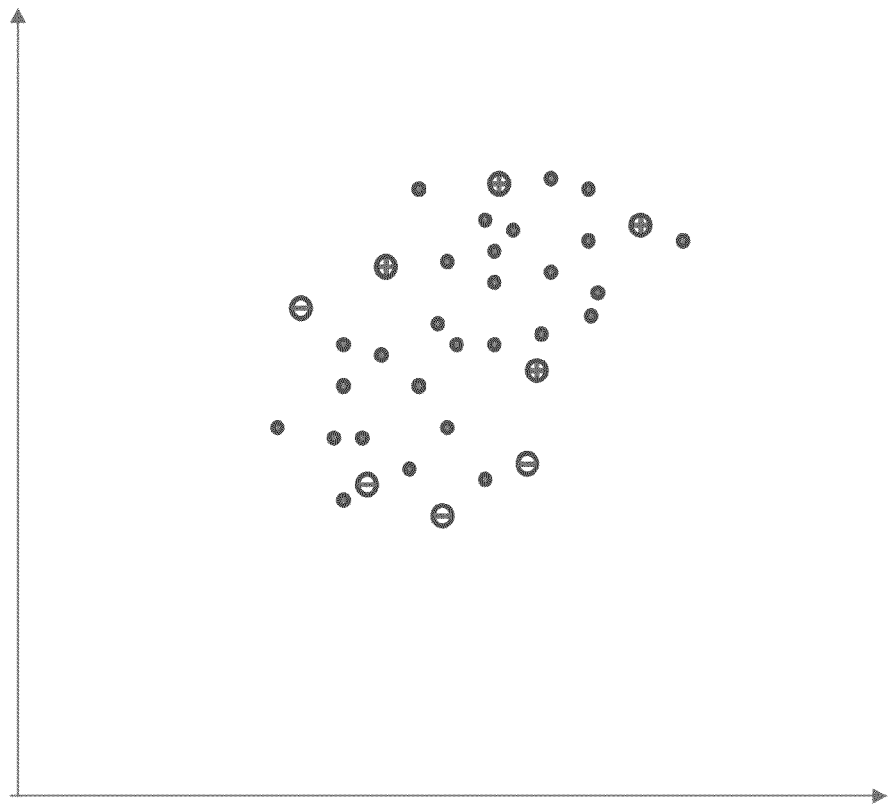
FIG. 7 is an exemplary graph depicting points representing chemical assays, in a Euclidean space, according to an exemplary embodiment of the present invention.

Reference is now made to FIG. 7, which is an exemplary graph depicting points representing chemical assays, in a Euclidean space, according to an exemplary embodiment of the present invention.

In a fourth exemplary method, according to an exemplary embodiment of the present invention, each assay of a chemical reaction is represented by a respective point positioned in a Euclidean space, as described in further detail hereinabove.

Though illustrated using FIG. 7 with two dimensions, the Euclidean space may have any number of dimensions.

Optionally, the space's number of dimensions may depend on variable number of each assay. For example, assays characterized by three variables, may be represented by points in a three dimensional Euclidean space.

As illustrated using FIG. 7, the Euclidean space includes points of known negative assays (with a minus sign), points of known positive assays (with a plus sign) and remaining points that need to be classified as positive or negative.

Figure 8:
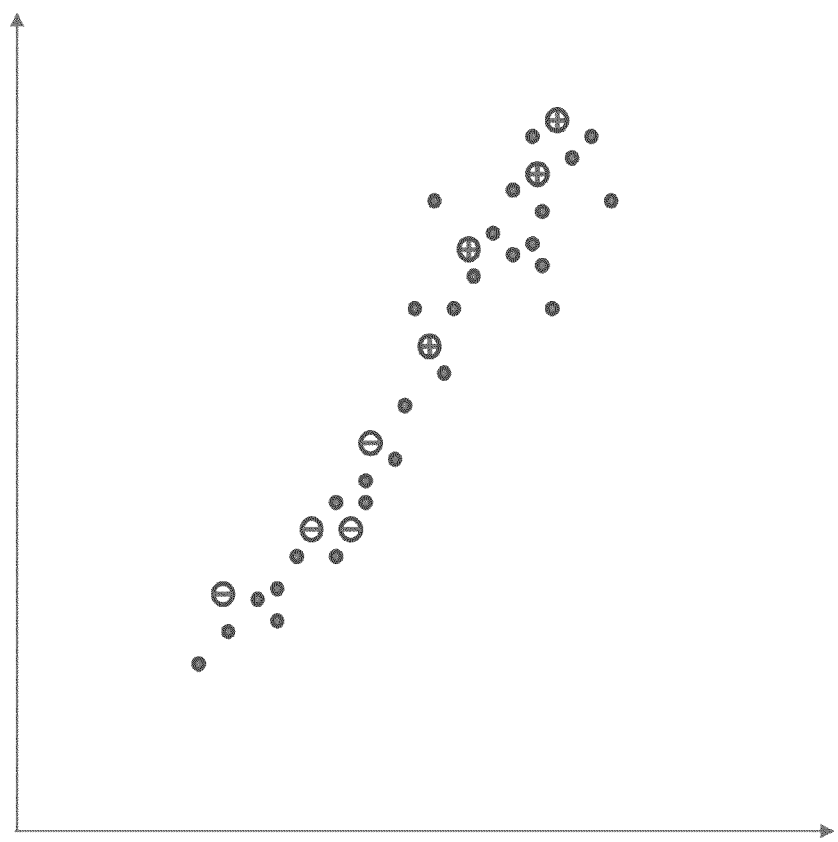
FIG. 8 is an exemplary graph depicting points representing chemical assays in a space calculated using diffusion mapping, according to an exemplary embodiment of the present invention.

Reference is now made to FIG. 8, which is an exemplary graph, depicting points representing chemical assays in a space calculated using diffusion mapping, according to an exemplary embodiment of the present invention.

In the fourth exemplary method according to an exemplary embodiment of the present invention, diffusion mapping is applied on the Euclidean space of FIG. 7, for calculating a dimensionality reduced space, as described in further detail hereinabove.

As illustrated using FIG. 8, the space calculated using diffusion mapping includes the same number of points of known negative assays (with a negative sign), points of known positive assays (with a positive sign) and remaining points that need to be classified as positive or negative.

However, in the calculated space, the points tend to concentrate in clearly recognizable two higher density areas.

Figure 9A:
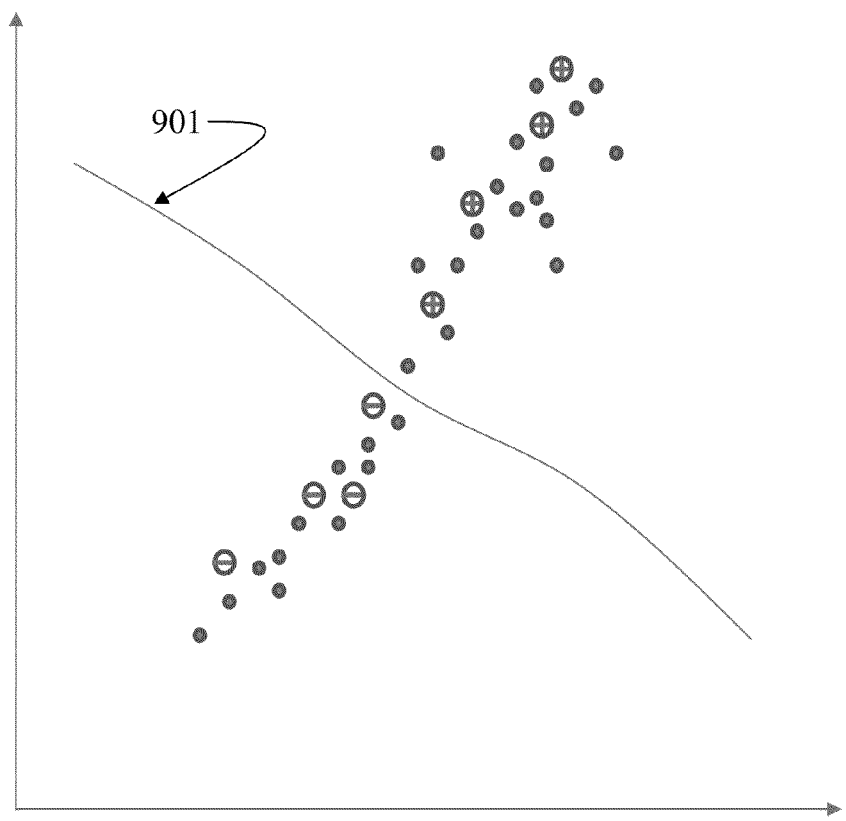
FIG. 9A is an exemplary graph depicting a function which defines a line and separates a calculated space into two groups, according to an exemplary embodiment of the present invention.

Reference is now made to FIG. 9A, which is an exemplary graph, depicting a function which defines a line and separates a calculated space into two groups, according to an exemplary embodiment of the present invention.

Optionally, in the exemplary fourth method, there is calculated a function 901 which defines a line. The function 901 divides the calculated space of FIG. 8, into two groups (Namely, a group of negative assays and a group of positive assays), say using SVM (Support Vector Machine), as described in further detail hereinabove.

Figure 9B:
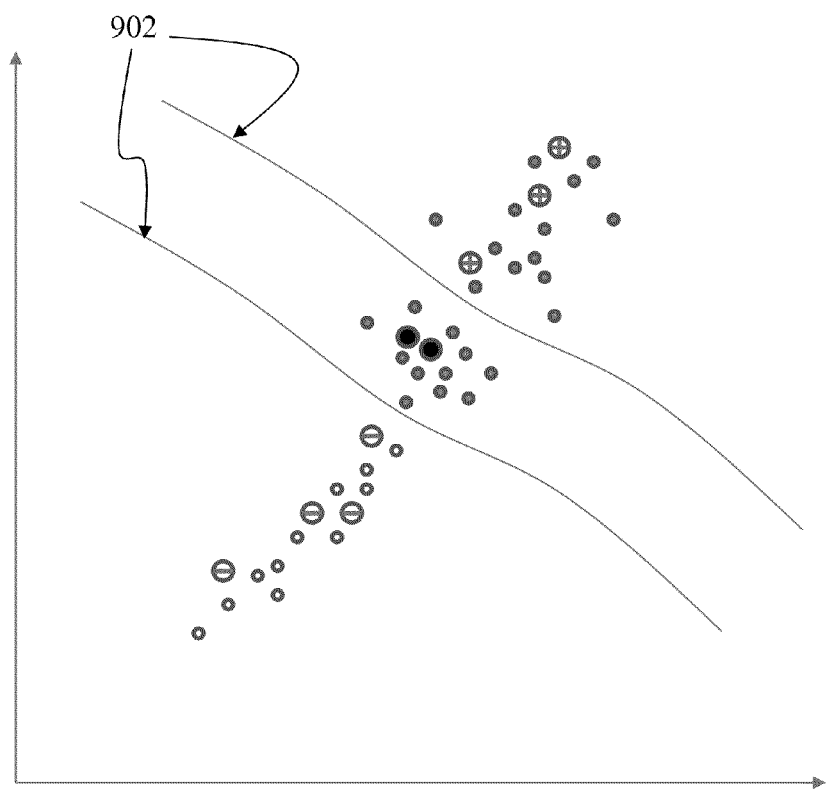
FIG. 9B is an exemplary graph depicting a function which defines two lines and separates a calculated space into three groups, according to an exemplary embodiment of the present invention.

Reference is now made to FIG. 9B, which is an exemplary graph, depicting a function which defines two lines and separates a calculated space into three groups, according to an exemplary embodiment of the present invention.

Optionally, in the fourth exemplary method, there is rather calculated a function 902 which defines two lines, and divides the calculated space of FIG. 8, into three groups.

With function 902, the groups include: a group of negative assays (which includes known negative assay points marked with a minus sign), a group of positive assays (which includes points marked with a plus sign), and a group of neutral assays (which includes points painted black).

Figure 9C:
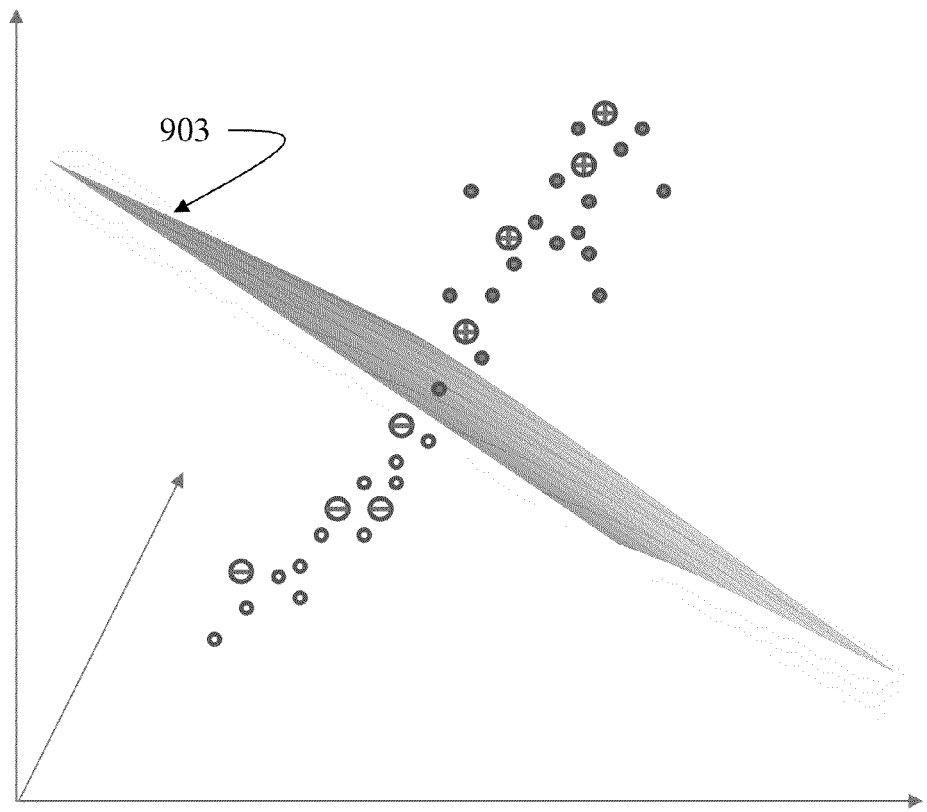
FIG. 9C is an exemplary graph depicting a function which defines a hyper-surface, and separates a calculated space into two groups, according to an exemplary embodiment of the present invention.

Reference is now made to FIG. 9C, which is an exemplary graph, depicting a function which defines a hyper-surface, and separates a calculated space into two groups, according to an exemplary embodiment of the present invention.

Optionally, in the fourth exemplary method, there is rather calculated a function 903 which defines a hyper-surface, and divides the calculated space of FIG. 8, into two groups (one negative and one positive), as described in further detail hereinabove.

Figure 10:
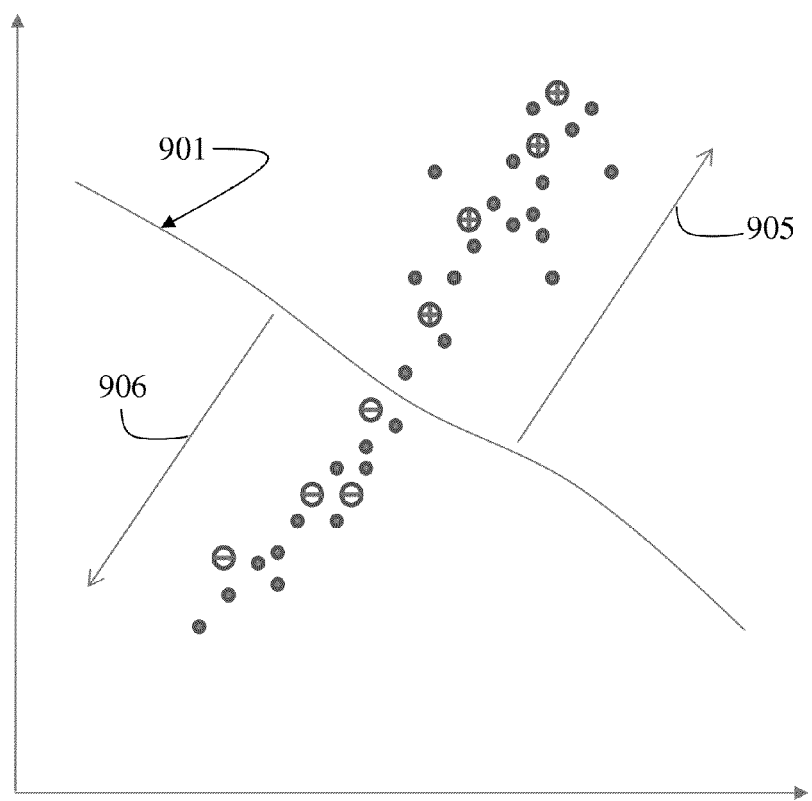
FIG. 10 is a second exemplary graph depicting the function which defines a line and separates the calculated space into the two groups, according to an exemplary embodiment of the present invention.

Reference is now made to FIG. 10, which is a second exemplary graph, depicting the function which defines a line and separates the calculated space into the two groups, according to an exemplary embodiment of the present invention.

Each of the points in the space (divided into the two groups) of FIG. 8, is positioned within a certain distance (as illustrated using arrows 905, 906) from the function 901 of FIG. 9A, which divides the calculated space into the two groups.

Optionally, the function 901 is calculated by SVM, and each point's distance from function 901 is given by the absolute value of the SVM discriminant function in the point, as described in further detail hereinabove.

Figure 11:
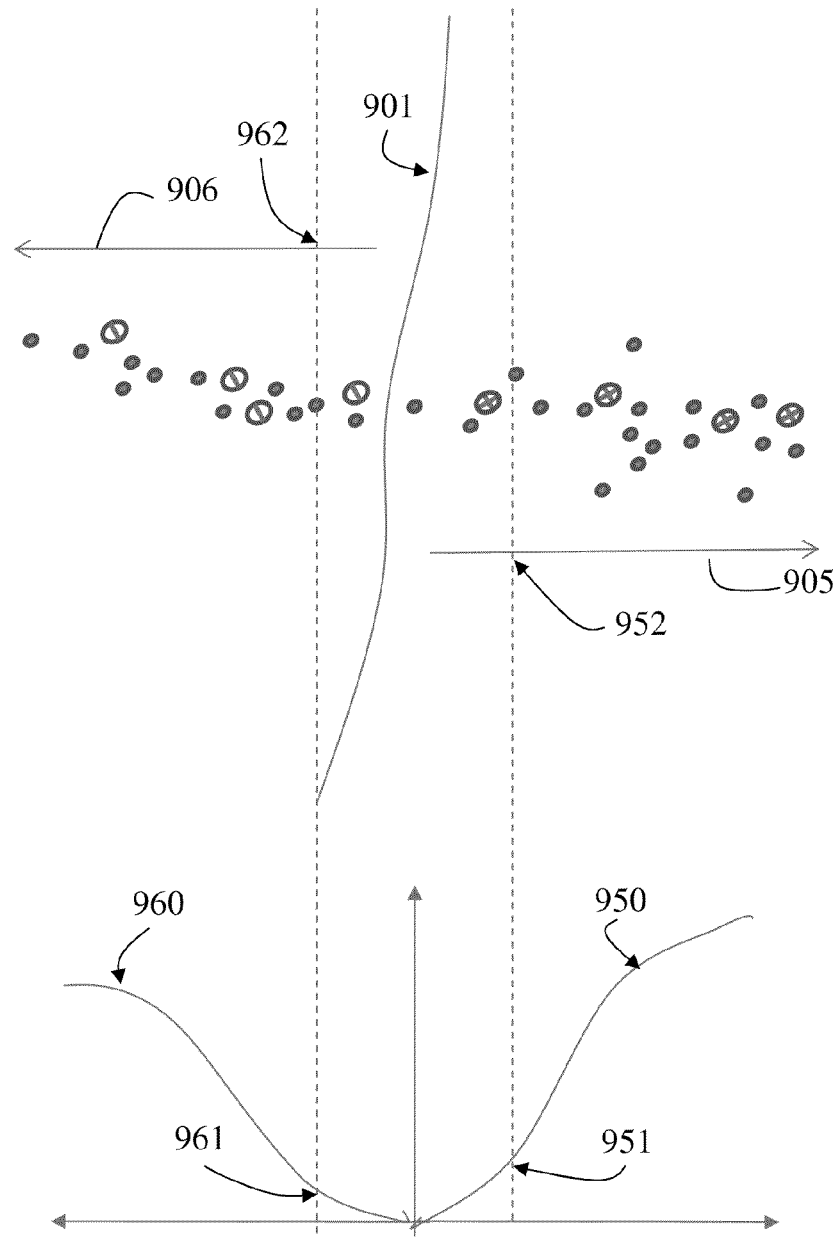
FIG. 11 is an exemplary graph depicting cumulative functions, according to an exemplary embodiment of the present invention.

Reference is now made to FIG. 11, which is an exemplary graph, depicting cumulative functions, according to an exemplary embodiment of the present invention.

Further in the fourth exemplary method, according to an exemplary embodiment of the present invention, there is calculated a first cumulative function 950.

The first cumulative function 950 gives a number of points on the calculated function's 901 (which divides the space into the two groups) positive side, as a function of distance 905 from the function 901.

Further in the fourth exemplary method, there is calculated a second cumulative function 960, which gives a number of points on the calculated function's 901 negative side, as a function of distance 906 from the function 901.

Optionally, the distance of each point from the function 901 which divides the space, is determined using conventional analytic geometry tools, by calculating the shortest distance (i.e. a normal) between the point and the function 901, as known in the art.

In each of the cumulative functions 950, 960, there is found an elbow point (i.e. a transition point), as described in further detail hereinabove.

A first elbow point 951 is found in the first cumulative function 950.

As shown, the first elbow point 951 is located in a distance 952 to the right of the function 901 which divides the space into the two groups.

A second elbow point 961 is found in the second cumulative function 960.

As shown, the second elbow point 961 is located in a distance 962 to the left of the function 901 which divides the space into the two groups.

Figure 12:
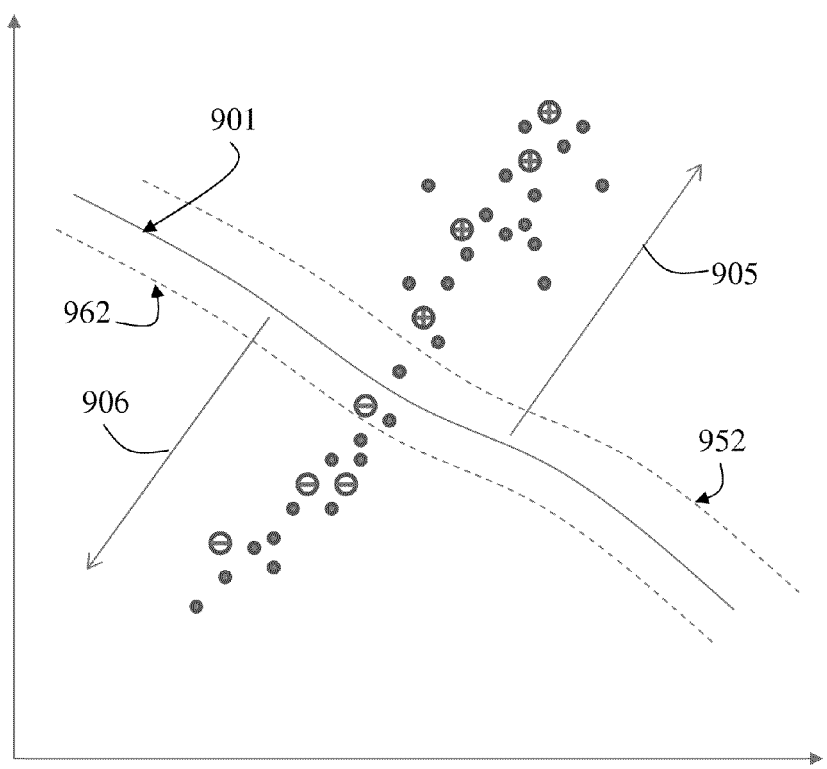
FIG. 12, which is an exemplary graph depicting thresholds based on transition points of a cumulative function, according to an exemplary embodiment of the present invention.

Reference is now made to FIG. 12, which is an exemplary graph, depicting thresholds based on transition points of a cumulative function, according to an exemplary embodiment of the present invention.

In the exemplary method, the distances 952, 962 of the found transition points (i.e. elbow points 951 and 961, respectively) from the function 901, are used as thresholds, for identifying outliers among the points (and thus identifying erroneous assays), as described in further detail hereinabove.

That is to say that points that are positioned between the thresholds 952, 962, are found to be outliers, as described in further detail hereinabove.

It is expected that during the life of this patent many relevant devices and systems will be developed and the scope of the terms herein, particularly of the terms "Computer", "Server", "Desktop computer", "Laptop computer", "Tablet computer", "Cellular phone", and "SaaS", is intended to include all such new technologies a priori.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. An apparatus for identifying outliers among chemical reaction assays, the apparatus comprising:
   a programmed computer;
   a transition point finder, implemented on the computer and configured to find at least one transition point in a cumulative function, the cumulative function being based on a count of points in a calculated space as a function of distance of the points from a function dividing the calculated space into at least two groups, each one of the points representing results of a respective assay of a chemical reaction; and
   an outlier identifier, in communication with said transition point finder, configured to use a distance of the found transition point from the function dividing the calculated space, as a threshold, for identifying an outlier among the chemical reaction assays.

2. The apparatus of claim 1, further comprising a cumulative function calculator, in communication with said transition point finder, configured to calculate the cumulative function.

3. The apparatus of claim 1, wherein the cumulative function gives a number of points in the calculated space as a function of the distance of the points from the function dividing the calculated space.

4. The apparatus of claim 1, wherein the cumulative function gives a density of points in the calculated space as a function of the distance of the points from the function dividing the calculated space.

5. The apparatus of claim 1, wherein the cumulative function is specific to one of the groups.

6. The apparatus of claim 1, wherein the cumulative function is common to at least two of the groups.

7. The apparatus of claim 1, wherein the function dividing the calculated space is a polynomial function.

8. The apparatus of claim 1, wherein the calculated space is a space enhancing proximity among points representing assays of qualitatively identical chemical reactions.

9. The apparatus of claim 1, further comprising a result receiver, configured to receive a plurality of sets of results, each one of the received sets of results pertaining to a respective assay of a chemical reaction, and a space calculator, configured to calculate the space, using the received sets of results.

10. The apparatus of claim 1, further comprising a space calculator, configured to calculate the space, using dimensionality reduction.

11. The apparatus of claim 1, further comprising a space calculator, configured to calculate the space, using diffusion mapping.

12. The apparatus of claim 1, further comprising a dividing function calculator, configured to calculate the function dividing the calculated space.

13. A computer implemented method for identifying outliers among chemical reaction assays, the method comprising steps the computer is programmed to perform, the steps comprising:
   by a programmed computer, finding at least one transition point in a cumulative function, the cumulative function being based on a count of points in a calculated space as a function of distance of the points from a function dividing the calculated space into at least two groups, each one of the points representing results of a respective assay of a chemical reaction; and
   using a distance of the found transition point from the function dividing the calculated space, as a threshold, for identifying an outlier among the chemical reaction assays.

14. The method of claim 13, further comprising a step of calculating the cumulative function.

15. The method of claim 13, wherein the cumulative function gives a number of points in the calculated space as a function of the distance of the points from the function dividing the calculated space.

16. The method of claim 13, wherein the cumulative function gives a density of points in the calculated space as a function of the distance of the points from the function dividing the calculated space.

17. The method of claim 13, wherein the cumulative function is specific to one of the groups.

18. The method of claim 13, wherein the cumulative function is common to at least two of the groups.

19. The method of claim 13, wherein the function dividing the calculated space is a polynomial function.

20. The method of claim 13, wherein the calculated space is a space enhancing proximity among points representing assays of qualitatively identical chemical reactions.

21. The method of claim 13, further comprising a step of receiving a plurality of sets of results, each one of the received sets of results pertaining to a respective assay of a chemical reaction, and calculating the space, using the received sets of results.

22. The method of claim 13, further comprising a step of calculating the space, using dimensionality reduction.

23. The method of claim 13, further comprising a step of calculating the space, using diffusion mapping.

24. The method of claim 13, further comprising a step of calculating the function dividing the calculated space.

25. A non-transitory computer readable medium storing computer executable instructions for performing steps of identifying outliers among chemical reaction assays, the steps comprising:

finding at least one transition point in a cumulative function, the cumulative function being based on a count of points in a calculated space as a function of distance of the points from a function dividing the calculated space into at least two groups, each one of the points representing results of a respective assay of a chemical reaction; and using a distance of the found transition point from the function dividing the calculated space, as a threshold, for identifying an outlier among the chemical reaction assays.

26. The computer readable medium of claim 25, wherein the steps further comprise a step of calculating the cumulative function.

* * * * *